US012733895B2

(12) United States Patent
Niibe

(10) Patent No.: US 12,733,895 B2
(45) Date of Patent: Sep. 15, 2026

(54) RADIOGRAPHIC SYSTEM AND METHOD FOR CONTROLLING THE SAME

(71) Applicant: CANON KABUSHIKI KAISHA, Tokyo (JP)

(72) Inventor: Yusuke Niibe, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 729 days.

(21) Appl. No.: 18/297,505

(22) Filed: Apr. 7, 2023

(65) Prior Publication Data

US 2023/0329663 A1 Oct. 19, 2023

(30) Foreign Application Priority Data

Apr. 14, 2022 (JP) ................................ 2022-067007

(51) Int. Cl.
*A61B 6/00* (2024.01)
*G01T 1/17* (2006.01)
*A61B 6/42* (2024.01)

(52) U.S. Cl.
CPC .................. *A61B 6/54* (2013.01); *A61B 6/56* (2013.01); *G01T 1/17* (2013.01); *A61B 6/4283* (2013.01); *A61B 6/4452* (2013.01); *A61B 6/542* (2013.01); *A61B 6/548* (2013.01)

(58) Field of Classification Search
CPC ........... A61B 6/54; A61B 6/56; A61B 6/4283; A61B 6/4452; A61B 6/542; A61B 6/548; G01T 1/17
See application file for complete search history.

(56) References Cited

U.S. PATENT DOCUMENTS

2015/0078528 A1* 3/2015 Okada .................... A61B 6/542 378/97

FOREIGN PATENT DOCUMENTS

| | | | |
|---|---|---|---|
| JP | 2003210445 | A | 7/2003 |
| JP | 2014044856 | A | 3/2014 |
| JP | 2014045938 | A | 3/2014 |
| JP | 2014178116 | A | 9/2014 |
| JP | 2015146916 | A | 8/2015 |
| JP | 2018126447 | A | 8/2018 |
| JP | 2019097750 | A | 6/2019 |
| JP | 2021178119 | A | 11/2021 |
| WO | 2013176251 | A1 | 11/2013 |
| WO | 2022064846 | A1 | 3/2022 |

* cited by examiner

*Primary Examiner* — Chih-Cheng Kao
(74) *Attorney, Agent, or Firm* — Canon U.S.A., Inc. IP Division

(57) ABSTRACT

A radiographic system includes a radiation generating apparatus that controls irradiation with radiation from a radiation source and a radiographic imaging apparatus that captures an image based on the radiation from the radiation source. The radiation generating apparatus and the radiographic imaging apparatus perform communication of irradiation control information and communication of synchronization information between each other using a same interface. The irradiation control information is used to control the irradiation with the radiation from the radiation source based on a dose of the radiation from the radiation source. The synchronization information is used to synchronize imaging timing between the radiation generating apparatus and the radiographic imaging apparatus.

14 Claims, 5 Drawing Sheets

Figure 2:
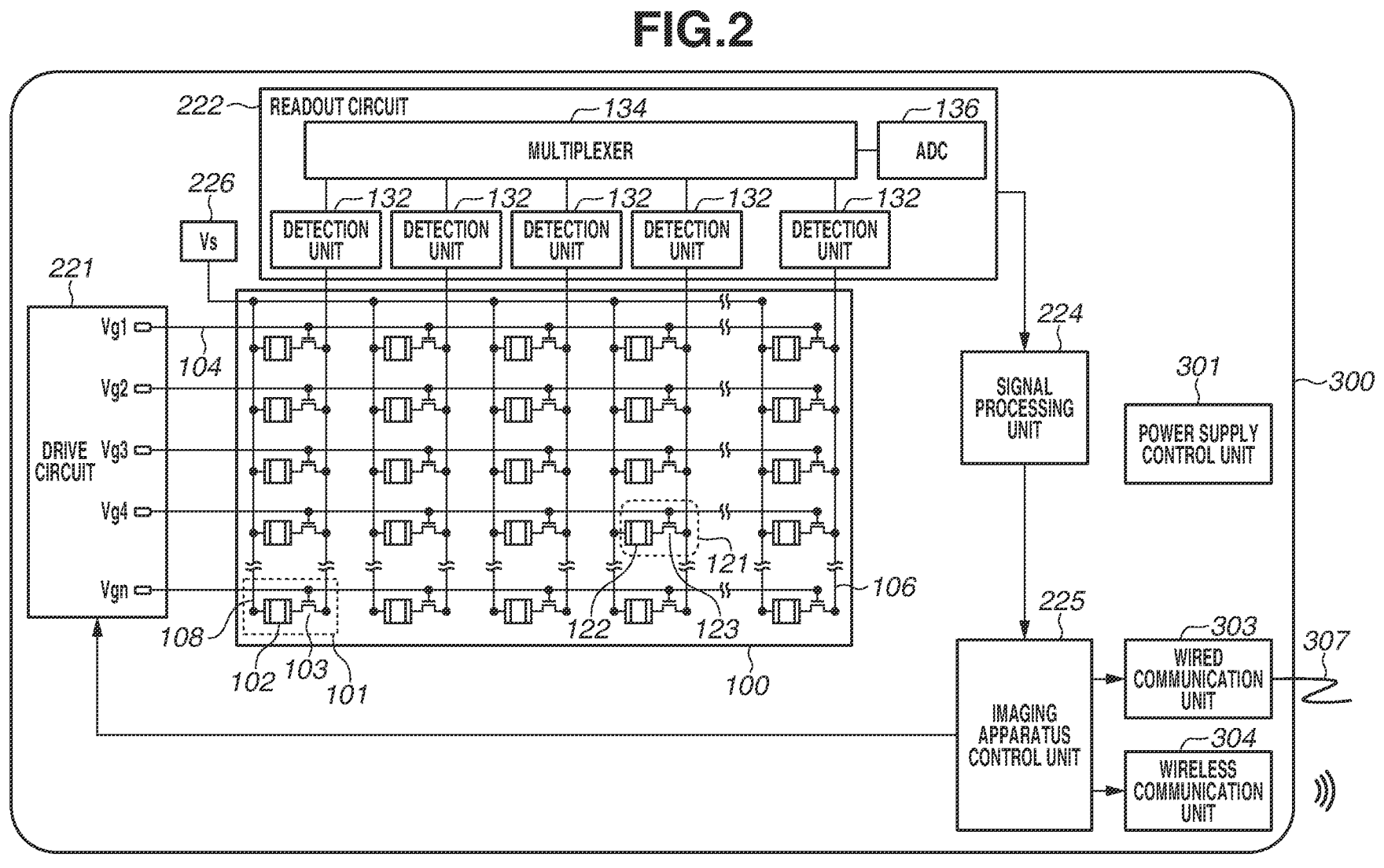

300
301 POWER SUPPLY CONTROL UNIT
303 WIRED COMMUNICATION UNIT
304 WIRELESS COMMUNICATION UNIT
307
224 SIGNAL PROCESSING UNIT
225 IMAGING APPARATUS CONTROL UNIT
222 READOUT CIRCUIT
134 MULTIPLEXER
136 ADC
132 DETECTION UNIT
226 Vs
221 DRIVE CIRCUIT
Vg1
Vg2
Vg3
Vg4
Vgn
100
101
102
103
104
106
108
121
122
123

1
2
20
300
301
302
303
304
306
307
310
311
312
313
314
315
316
320
323
324
325
326
327

RADIOGRAPHIC SYSTEM AND METHOD FOR CONTROLLING THE SAME

BACKGROUND

Field

The present disclosure relates to a radiographic system and a method for controlling the radiographic system.

Description of the Related Art

A radiographic apparatus and a radiographic system, which use a sensor panel that detects radiation such as X-rays, have been widely used in the industrial field and the medical field. An apparatus that uses a two-dimensional solid-state image sensor for an image receptor (a radiation detector) is generally used for such radiographic apparatuses. The two-dimensional solid-state image sensor generally repeats an operation of accumulating charges corresponding to incident light, reading out the accumulated charges, and resetting the charges. In the case of a solid-state image sensor without an electronic shutter, there is a possibility of impairment of images to be obtained if light is incident on the solid-state image sensor during the readout or resetting of the charges. In particular, in a medical radiographic apparatus, the light incidence brings about disadvantageous effects such as unnecessary exposure. Thus, the radiographic system operates while synchronizing the operation timing of the solid-state image sensor of the image receptor (the radiation detector) and the radiation irradiation timing of a radiation generating apparatus.

In recent years, a study of multifunctionality of radiographic apparatuses has been conducted. As part of the study, incorporation of a radiation irradiation monitoring function into a radiographic apparatus has been studied. This function enables, for example, detection of timing at which radiation irradiation from a radiation source is started, detection of timing at which the radiation irradiation is to be stopped, and detection of a radiation irradiation amount or an integrated irradiation amount. Automatic exposure control (AEC) can also be performed by detection of the integrated irradiation amount of radiation transmitted through a subject, and stopping of the radiation irradiation from the radiation source when the detected integrated irradiation amount reaches a proper amount. In a case where the automatic exposure control is performed using a flat panel detector (FPD), a plate-like AEC sensor, which is provided separately from the FPD, is generally located to be sandwiched between the subject and the FPD. The AEC sensor measures the dose of the radiation transmitted through the subject in predetermined one to five radiation detection areas (receptor fields) for radiation monitoring, and performs control to stop X-ray irradiation when the measured dose reaches a predetermined dose.

Japanese Patent Application Laid-Open No. 2014-45938 discusses a radiographic system that includes a radiographic imaging apparatus having pixels for monitoring radiation irradiation, a radiation source, and a radiation source controller. When detecting the timing at which the irradiation is to be stopped, the radiographic system transmits an irradiation stop signal from the radiographic imaging apparatus to an X-ray generation apparatus. The radiographic system also transmits a signal for automatic exposure control from the radiographic imaging apparatus to the radiation source controller using an interface for an AEC sensor separate from an FPD, without using an interface for synchronization, thereby implementing an AEC function.

Japanese Patent Application Laid-Open No. 2014-45938 has an issue where a radiographic system that does not include the interface for the AEC sensor separate from the FPD is not taken into consideration.

SUMMARY

The present disclosure is directed to a technique for enabling communication for automatic exposure control without adding an interface.

According to an aspect of the present disclosure, a radiographic system includes a radiation generating apparatus configured to control irradiation with radiation from a radiation source, and a radiographic imaging apparatus configured to capture an image based on the radiation from the radiation source. The radiation generating apparatus and the radiographic imaging apparatus are configured to perform communication of irradiation control information and communication of synchronization information between each other using a same interface. The irradiation control information is used to control the irradiation with the radiation from the radiation source based on a dose of the radiation from the radiation source. The synchronization information is used to synchronize imaging timing between the radiation generating apparatus and the radiographic imaging apparatus.

Further features will become apparent from the following description of exemplary embodiments with reference to the attached drawings.

BRIEF DESCRIPTION OF THE DRAWINGS

FIG. 2 is a diagram illustrating a configuration example of a radiographic imaging apparatus.

DESCRIPTION OF THE EMBODIMENTS

Figure 1:
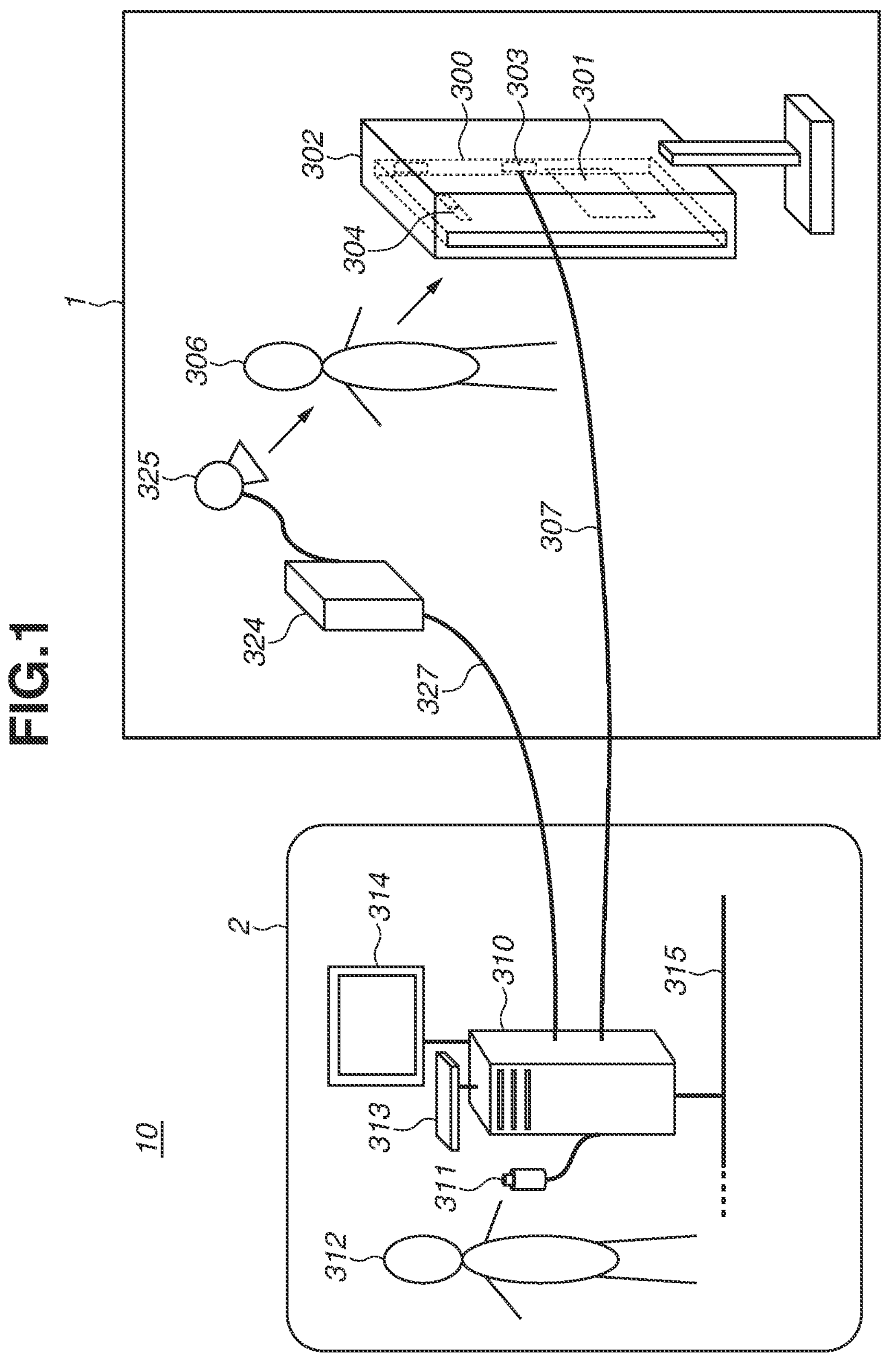
FIG. 1 is a diagram illustrating a configuration example of a radiographic system.

FIG. 1 is a diagram illustrating a configuration example of a radiographic system 10 according to an exemplary embodiment of the present disclosure. The radiographic system 10 is installed in a radiation room 1 and a control room 2. In the radiation room 1, radiographic imaging is performed by radiation irradiation. The control room 2 is located remote from the radiation room 1.

In the radiation room 1, the radiographic system 10 includes a radiographic imaging apparatus 300, an upright position stand 302, a radiographic imaging apparatus communication cable 307, a radiation generating apparatus 324, a radiation source 325, and a radiation generating apparatus communication cable 327. In the control room 2, the radiographic system 10 includes a control apparatus 310, a radiation irradiation switch 311, an input apparatus 313, a display apparatus 314, and an in-hospital local area network (LAN) 315.

The radiographic imaging apparatus 300 includes a power supply control unit 301, which includes a battery (not illustrated), a wired communication unit 303, and a wireless communication unit 304. The radiographic imaging apparatus 300 detects radiation emitted from the radiation source 325 and is transmitted through a subject 306, and generates radiographic image data. The wired communication unit 303 enables exchange of information, for example, by connecting to a cable using a communication standard having predetermined rules or a standard, such as Ethernet.

The wireless communication unit 304 includes, for example, an antenna and a circuit board that includes a communication integrated circuit (IC). The circuit board including the communication IC performs wireless communication processing according to a wireless LAN protocol via the antenna. The frequency band, standard, and method to be used for wireless communication are not specifically limited. Examples of the method include short-range wireless communication such as near-field communication (NFC), Bluetooth®, and an ultra-wideband (UWB). The wireless communication unit 304 can also employ a plurality of wireless communication methods and perform communication by selecting a method as appropriate.

The upright position stand 302 is a stand in which the radiographic imaging apparatus 300 is mounted and that enables radiographic imaging in an upright position. The radiographic imaging apparatus 300 is detachably mounted in the upright position stand 302, and can perform imaging in either the mounted state or the detached state. The radiographic imaging apparatus communication cable 307 is used to connect the wired communication unit 303 of the radiographic imaging apparatus 300 and the control apparatus 310.

The radiation generating apparatus 324 controls radiation irradiation from the radiation source 325 based on a predetermined irradiation condition. The radiation source 325 irradiates the subject 306 with radiation under control of the radiation generating apparatus 324.

The radiation generating apparatus communication cable 327 is used to connect the radiation generating apparatus 324 and the control apparatus 310. While the connection using the radiation generating apparatus communication cable 327 has been described as an example of the connection between the radiation generating apparatus 324 and the control apparatus 310, the connection can be implemented by a configuration that partially uses wireless communication. The radiation generating apparatus communication cable 327 can be a simple signal line, can implement communication according to a standard such as a serial communication standard or an Ethernet communication standard, or can simultaneously implement these communication methods.

The control apparatus 310 communicates with the radiation generating apparatus 324 and the radiographic imaging apparatus 300, and performs centralized control of the radiographic system 10. The radiation irradiation switch 311 inputs radiation irradiation timing in response to an operation performed by an operator 312.

The input apparatus 313 is used to input an instruction from the operator 312, and various kinds of input devices such as a keyboard and/or a touch panel are used for the input apparatus 313. The display apparatus 314 displays radiographic image data subjected to image processing and a graphical user interface (GUI), and a display or the like is used as the display apparatus 314. The in-hospital LAN 315 is a backbone network in the hospital.

FIG. 2 is a diagram illustrating a configuration example of the radiographic imaging apparatus 300 illustrated in FIG. 1. The radiographic imaging apparatus 300 includes a radiation detector 100, a drive circuit 221, a readout circuit 222, a signal processing unit 224, an imaging apparatus control unit 225, an element power supply circuit 226, a power supply control unit 301, the wired communication unit 303, and the wireless communication unit 304.

The radiation detector 100 has a function of detecting radiation irradiation. The radiation detector 100 includes a plurality of pixels arranged in a plurality of rows and a plurality of columns. In the following description, an area of the radiation detector 100 in which the plurality of pixels is arranged is referred to as a detection area.

The plurality of pixels includes imaging pixels (hereinafter referred to as detection pixels) 101 for acquisition of a radiographic image or acquisition of radiation irradiation information, and correction pixels 121 for removal of dark current components and crosstalk components.

The detection pixels 101 can be used just for the acquisition of a radiographic image or just for the acquisition of radiation irradiation information. In another exemplary embodiment, the detection pixels 101 can be used for the acquisition of a radiographic image or the acquisition of radiation irradiation information. In still yet another exemplary embodiment, the detection pixels 101 can be used simultaneously for the acquisition of a radiographic image and the acquisition of radiation irradiation information.

Each of the detection pixels 101 includes a first conversion element 102 that converts radiation into an electric signal, and a first switch 103 that is arranged between one of column signal lines 106 and the first conversion element 102. The first conversion element 102 includes a scintillator that converts radiation into light, and a photoelectric conversion element that converts light into an electric signal. The first switch 103 is, for example, a semiconductor such as amorphous silicon or polysilicon (desirably polysilicon), and includes a thin film transistor (TFT) where an active area is formed. The scintillator is generally formed into a sheet-like shape to cover the detection area, and is shared by a plurality of pixels. In another exemplary embodiment, the first conversion element 102 includes a conversion element that directly converts radiation into an electric signal.

The correction pixels 121 are used to remove dark current components and crosstalk components, and each include a second conversion element 122 and a second switch 123. The second conversion element 122 has a configuration basically similar to that of the first conversion element 102, but is different from the first conversion element 102 in sensitivity for detection of incident radiation. For example, the second conversion element 122 has a smaller area for detection of radiation and lower sensitivity for detection of radiation than the first conversion element 102. The area for detection of radiation can be made smaller by, for example, providing a shield member to block radiation using heavy metal, such as lead, on the second conversion element 122.

The area in which the detection pixels 101 and the correction pixels 121 are arranged is provided at any position of the radiation detector 100. The radiographic imaging apparatus 300 includes the plurality of column signal lines 106 and a plurality of drive lines 104. Each of the column signal lines 106 corresponds to a different one of the plurality of columns in the radiation detector 100. Each of the drive lines 104 corresponds to a different one of the plurality of rows in the radiation detector 100. The drive lines 104 are driven by voltages Vg1 to Vgn of the drive circuit 221, and perform on-off control of the first switches 103 and the second switches 123.

A first electrode of the first conversion element 102 and a first electrode of the second conversion element 122 are connected to a first main electrode of the first switch 103 and a first main electrode of the second switch 123, respectively. A second electrode of the first conversion element 102 and a second electrode of the second conversion element 122 are connected to one of bias lines 108.

Each of the bias lines 108 extends in a column direction, and is connected in common to the second electrodes of the plurality of first conversion elements 102 and the second electrodes of the plurality of second conversion elements 122 arranged in the corresponding column. The bias lines 108 receive a bias voltage Vs from the element power supply circuit 226. The bias voltage Vs is supplied from the element power supply circuit 226.

The power supply control unit 301 includes a battery and a direct current-direct current (DC-DC) converter. The power supply control unit 301 includes a power supply circuit, and generates an analog circuit power supply voltage and a digital circuit power supply voltage for drive control, communication, and the like.

Second main electrodes of the first switches 103 of the plurality of detection pixels 101 and second main electrodes of the second switches 123 of the plurality of correction pixels 121 arranged in each column are connected to a corresponding one of the column signal lines 106. Control electrodes of the first switches 103 of the plurality of detection pixels 101 and control electrodes of the second switches 123 of the plurality of correction pixels 121 arranged in each row are connected to a corresponding one of the drive lines 104. The drive circuit 221 selectively changes the voltages Vg1 to Vgn to a high level in a predetermined order to turn on the first switches 103 and the second switches 123 connected to the drive line 104 in one row. As a result, signals of the first conversion elements 102 and the second conversion elements 122 in one row are output to the corresponding column signal lines 106 in the respective columns.

The plurality of column signal lines 106 is connected to the readout circuit 222. The readout circuit 222 described herein includes a plurality of detection units 132, a multiplexer 134, and an analog-to-digital converter (hereinafter referred to as an AD converter or an ADC) 136.

Each of the plurality of column signal lines 106 is connected to a corresponding one of the plurality of detection units 132 in the readout circuit 222. Each of the column signal lines 106 corresponds to a different one of the detection units 132. The detection units 132 each include, for example, a differential amplifier that amplifies signals from the corresponding column signal line 106. The multiplexer 134 selects the plurality of detection units 132 in a predetermined order, and supplies signals from the selected detection unit 132 to the AD converter 136. The AD converter 136 converts the supplied signals into digital signals, and outputs the digital signals to the signal processing unit 224.

The signal processing unit 224 outputs radiation irradiation information of the radiographic imaging apparatus 300 based on the output from the readout circuit 222 (the AD converter 136). More specifically, the signal processing unit 224 performs, for example, characteristic correction processing to remove dark current components and crosstalk components of the radiographic imaging apparatus 300 using the correction pixels 121, detection of radiation irradiation, and calculation of a radiation irradiation amount and an integrated irradiation amount.

The imaging apparatus control unit 225 controls the drive circuit 221, the readout circuit 222, and the like, based on information from the signal processing unit 224 or a control command from the control apparatus 310 illustrated in FIG. 1. The wired communication unit 303 communicates with the control apparatus 310 illustrated in FIG. 1 via the radiographic imaging apparatus communication cable 307 under control of the imaging apparatus control unit 225. The wireless communication unit 304 performs wireless communication under control of the imaging apparatus control unit 225.

Figure 3:
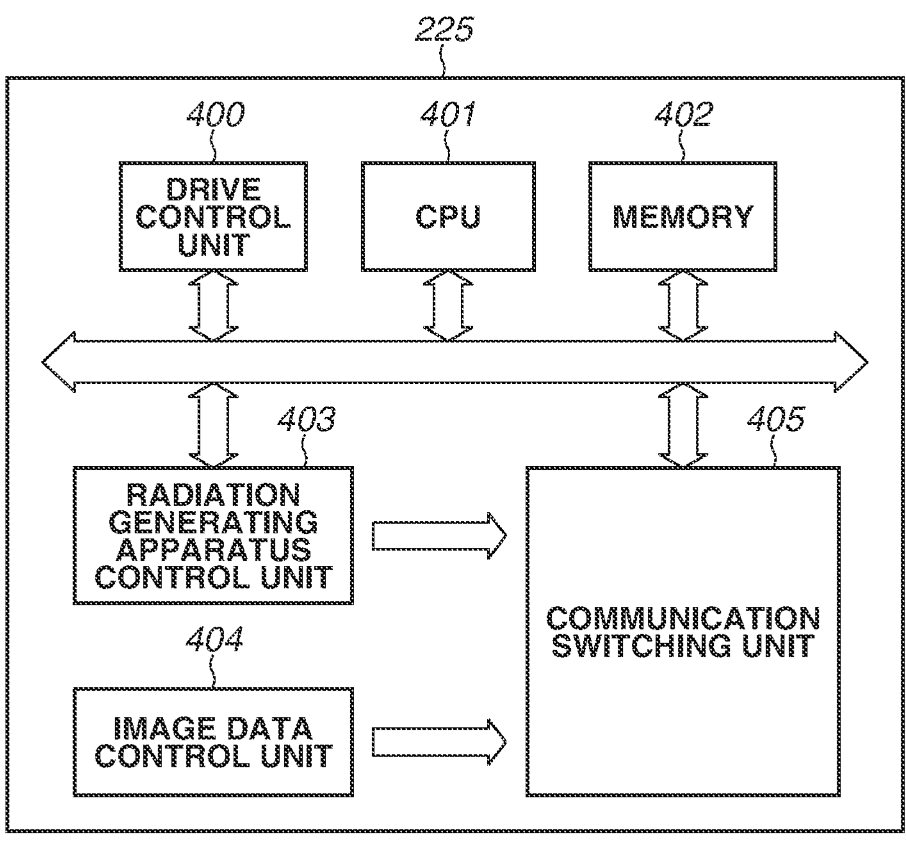
FIG. 3 is a diagram illustrating a configuration example of an imaging apparatus control unit in the radiographic imaging apparatus.

FIG. 3 is a diagram illustrating a configuration example of the imaging apparatus control unit 225 of the radiographic imaging apparatus 300. The imaging apparatus control unit 225 includes a drive control unit 400, a central processing unit (CPU) 401, a memory 402, a radiation generating apparatus control unit 403, an image data control unit 404, and a communication switching unit 405. The drive control unit 400 controls the drive circuit 221 and the readout circuit 222, which are illustrated in FIG. 2, based on information from the signal processing unit 224 illustrated in FIG. 2 and a command from the control apparatus 310 illustrated in FIG. 1.

The CPU 401 controls the radiographic imaging apparatus 300 using a program and various kinds of data stored in the memory 402. The memory 402 stores, for example, a program and various kinds of data to be used by the CPU 401 to execute processing. The various kinds of data include data obtained by processing of the CPU 401 and radiographic image data.

The radiation generating apparatus control unit 403 controls communication with the radiation generating apparatus 324 illustrated in FIG. 1 based on information from the signal processing unit 224 illustrated in FIG. 2 and information from the drive control unit 400. The radiation generating apparatus control unit 403 and the radiation generating apparatus 324 exchange information regarding control of the radiation generating apparatus 324, e.g., a radiation irradiation start notification, a radiation irradiation stop notification, a radiation irradiation amount, and an integrated irradiation amount.

When the radiation irradiation amount in a radiation detection area (a receptor field) for monitoring radiation reaches a reference threshold, the radiation generating apparatus control unit 403 provides the stop notification in the information about control of the radiation generating apparatus 324 to the radiation generating apparatus 324 via the control apparatus 310.

The radiation generating apparatus control unit 403 has a function (hereinafter referred to as a received dose monitoring function) of providing the stop notification when the radiation irradiation amount in the receptor field selected as a monitoring target reaches the reference threshold. In a case where a plurality of receptor fields is selected as monitoring targets, the radiation generating apparatus control unit 403 can execute a mode of providing the stop notification when the radiation irradiation amount in one of the selected receptor fields reaches the reference threshold. In another exemplary embodiment, the radiation generating apparatus control unit 403 can execute a mode of providing the stop notification when the radiation irradiation amount in every selected receptor field reaches the reference threshold. The mode in which the radiation generating apparatus control unit 403 provides the stop notification is set, for example, by the radiographic imaging apparatus 300, the radiation generating apparatus 324, or the control apparatus 310.

The image data control unit 404 performs control to store, in the memory 402, radiographic image data based on information output from the signal processing unit 224 illustrated in FIG. 2, and also performs control to communicate with the control apparatus 310. The image data control unit 404 and the control apparatus 310 exchange radiographic image data and control-related information (e.g., control commands) with each other.

The communication switching unit 405 switches between enabling communication of the wired communication unit 303 when the radiographic imaging apparatus communication cable 307 is connected to the radiographic imaging apparatus 300, and enabling communication of the wireless communication unit 304 when the radiographic imaging apparatus communication cable 307 is disconnected from the radiographic imaging apparatus 300.

Figure 4:
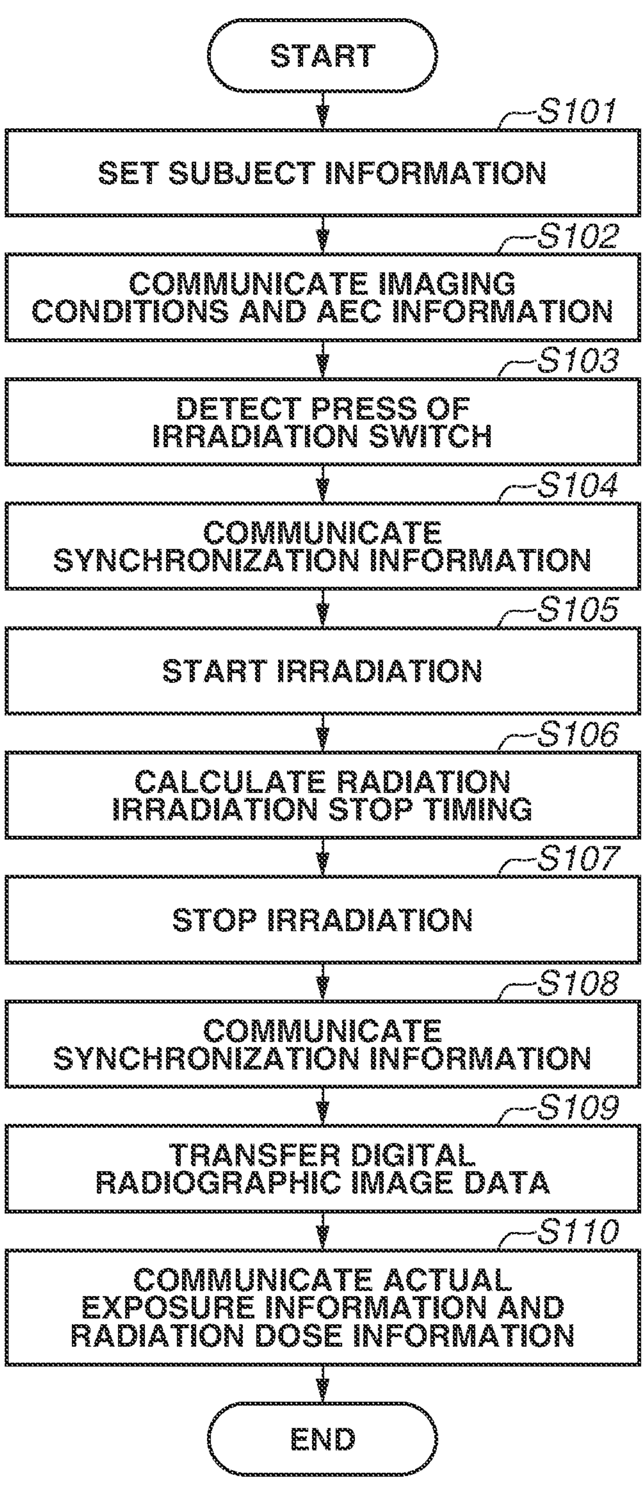
FIG. 4 is a flowchart illustrating a method for controlling the radiographic system.

FIG. 4 is a flowchart illustrating an example of a method for controlling the radiographic system 10 at the time of imaging. When the radiographic system 10 is powered on and the radiographic imaging apparatus 300 is powered on, the radiographic imaging apparatus 300 makes initial settings, and can thereby communicate with the control apparatus 310.

In step S101, the control apparatus 310 sets information about the subject 306, such as an identifier (ID), a name, and a birth date of the subject 306, based on an operation performed by the operator 312.

In step S102, the operator 312 fixes the posture of the subject 306 and that of the radiographic imaging apparatus 300. The operator 312 inputs, to the control apparatus 310, imaging conditions including a body part code of the subject 306, a tube voltage, a tube current, an irradiation time, a maximum permissible irradiation time, physical size information, a focal length, and automatic exposure control (AEC) setting information. The operator 312 also inputs, to the control apparatus 310, AEC information including information about whether an AEC function is used, a density in AEC, sensitivity in the AEC, receptor field information in the AEC, and a target dose in the AEC.

The information about the subject 306 and the AEC information can be automatically set, for example, by selection of an examination order received via the in-hospital LAN 315, or selection of a predetermined imaging protocol. In another exemplary embodiment, the information about the subject 306, the imaging conditions, and the AEC information can be directly input by the operator 312.

The control apparatus 310 transmits both the input imaging conditions and the input AEC information to the radiation generating apparatus 324 via the radiation generating apparatus communication cable 327 and to the radiographic imaging apparatus 300 via the radiographic imaging apparatus communication cable 307. The radiation generating apparatus 324 can receive the imaging conditions and the AEC information, and can control radiation irradiation. For example, the radiation generating apparatus 324 can change the control of radiation irradiation based on the AEC information (whether the AEC function is used). The radiographic imaging apparatus 300 can receive the imaging conditions and the AEC information, and can control imaging.

The radiographic imaging apparatus 300 can, for example, change the driving of the radiation detector 100 based on the imaging conditions (the maximum permissible irradiation time).

In another exemplary embodiment, the operator 312 can input the imaging conditions and the AEC information to the radiation generating apparatus 324. In this case, the radiation generating apparatus 324 transmits the imaging conditions and the AEC information to the control apparatus 310 via the radiation generating apparatus communication cable 327, and the control apparatus 310 transmits the imaging conditions and the AEC information to the radiographic imaging apparatus 300 via the radiographic imaging apparatus communication cable 307.

In step S103, when an imaging preparation is completed, the operator 312 selects the radiation irradiation switch 311. When the control apparatus 310 detects selection of the radiation irradiation switch 311, the processing proceeds to step S104.

In step S104, the radiographic imaging apparatus 300 communicates with the radiation generating apparatus 324 and performs control to start radiation irradiation. When the radiation irradiation switch 311 is selected, the radiation generating apparatus 324 transmits synchronization start information for start of synchronization of radiation irradiation to the radiographic imaging apparatus 300 via the control apparatus 310. Upon receiving the synchronization start information, the radiographic imaging apparatus 300 performs a preparation operation for incidence of radiation, starts accumulation of charges based on radiation, and notifies the radiation generating apparatus 324 of completion of the preparation for incidence of radiation via the control apparatus 310.

The radiographic imaging apparatus 300 can continuously transmit a signal to disable radiation irradiation to the radiation generating apparatus 324 via the control apparatus 310, and switch to transmitting a signal to enable radiation irradiation upon completion of the preparation for incidence of radiation. In this case, the radiation generating apparatus 324 determines that the synchronization start information is received in response to detection of switching from receiving the signal to disable radiation irradiation to receiving the signal to enable radiation irradiation. In other words, in step S104, the synchronization start information is communicated between the radiation generating apparatus 324 and the radiographic imaging apparatus 300.

In step S105, after receiving the notification of the completion of the preparation for incidence of radiation from the radiographic imaging apparatus 300, the radiation source 325 irradiates the subject 306 with radiation. The radiation with which the subject 306 is irradiated is transmitted through the subject 306 and is incident on the radiographic imaging apparatus 300.

The radiographic imaging apparatus 300 accumulates charges based on the radiation.

In step S106, the radiographic imaging apparatus 300 causes the detection pixels 101 to detect the radiation incident on the receptor field using the received dose monitoring function, and causes the signal processing unit 224 to calculate an integrated irradiation amount, which is an integrated value of doses (received doses) detected in a predetermined time period. The imaging apparatus control unit 225 calculates a reference threshold (radiation irradiation stop timing) based on the integrated irradiation amount from the signal processing unit 224, and the body part information, the imaging conditions, and the like input by the operator 312 based on the mode set in the radiation generating apparatus control unit 403.

In step S107, when the integrated irradiation amount reaches the reference threshold, the radiographic imaging apparatus 300 notifies the radiation generating apparatus 324 of an irradiation stop signal via the radiographic imaging apparatus communication cable 307, the control apparatus 310, and the radiation generating apparatus communication cable 327. Upon receiving the irradiation stop signal, the radiation generating apparatus 324 stops the radiation irradiation. The radiographic imaging apparatus 300 provides the notification of the irradiation stop signal as a radiation detection result, this is not seen to be limiting. In another exemplary embodiment, the radiographic imaging apparatus 300 can transmit information about the received dose in each predetermined time as the detection result, and the radiation generating apparatus 324 can calculate the integrated value of the received doses.

In step S108, the radiation generating apparatus 324 transmits a notification that the radiation irradiation is stopped to the radiographic imaging apparatus 300 via the control apparatus 310. Upon receiving the notification, the radiographic imaging apparatus 300 stops the accumulation of charges based on the radiation, and transmits synchronization end information to the radiation generating apparatus 324 via the control apparatus 310.

In step S108, in another exemplary embodiment, the radiation generating apparatus 324 does not transmit the notification that the irradiation is stopped to the radiographic imaging apparatus 300 even when the maximum permissible irradiation times elapses. In this embodiment, when the maximum permissible irradiation time elapses, the radiographic imaging apparatus 300 transmits the synchronization end information to the radiation generating apparatus 324 without waiting for the notification from the radiation generating apparatus 324.

The radiographic imaging apparatus 300 converts incident radiation into visible light and then detects the visible light as radiographic image signals using the photoelectric conversion elements until the radiation irradiation is stopped. The radiographic imaging apparatus 300 drives the photoelectric conversion elements to read out the radiographic image signals, causes the AD converter 136 to convert the analog signals into digital signals, thereby obtaining digital radiographic image data.

In step S109, the radiographic imaging apparatus 300 transfers the digital radiographic image data to the control apparatus 310 via the radiographic imaging apparatus communication cable 307. The control apparatus 310 performs image processing on the received digital radiographic image data. The control apparatus 310 displays, on the display apparatus 314, a radiographic image based on the radiographic image data subjected to the image processing. The control apparatus 310 functions as an image processing apparatus and a display control apparatus.

In step S110, after stopping the radiation irradiation, the radiation generating apparatus 324 transmits actual exposure information to the control apparatus 310. The actual exposure information includes a tube voltage, a tube current, an irradiation time, a tube current-time product, a focal point-to-subject distance, and a focal point-to-detector distance. The radiation generating apparatus 324 also receives dose information from a dosimeter (not illustrated) attached to the radiation source 325, and transmits the dose information to the control apparatus 310. The dose information includes an irradiation dose, an absorbed dose, an area dose, air kerma, and a skin dose. The dosimeter can directly transmit the dose information to the control apparatus 310 bypassing the radiation generating apparatus 324. In a case where the dosimeter is not attached to the radiation source 325, the radiation generating apparatus 324 can calculate the dose information based on the actual exposure information and transmit the dose information to the control apparatus 310. In a case where the radiation generating apparatus 324 does not have a function of calculating the dose information, the control apparatus 310 can calculate the dose information from the received actual exposure information. In a case where the control apparatus 310 calculates the dose information, the control apparatus 310 can transmit the dose information to the radiation generating apparatus 324, and the radiation generating apparatus 324 can display the dose information on a dose information display unit (not illustrated). The control apparatus 310 associates the actual exposure information and the dose information with the radiographic image data, and displays this information on the display apparatus 314.

As described above, the radiographic imaging apparatus 300 incorporating the AEC function can be adopted to the radiation generating apparatus 324 and the control apparatus 310 that are not provided with an interface for a separately provided AEC sensor. This eliminates the need to additionally provide the interface for the AEC in the radiation generating apparatus 324 and the control apparatus 310, and can save effort and cost for modifying the radiation generating apparatus 324 and the control apparatus 310.

The present exemplary embodiment describes an example using a configuration where the radiographic imaging apparatus communication cable 307 is directly connected to the control apparatus 310 for the purpose of communication between the radiographic imaging apparatus 300 and the control apparatus 310. This configuration is not seen to be limiting.

Figure 5:
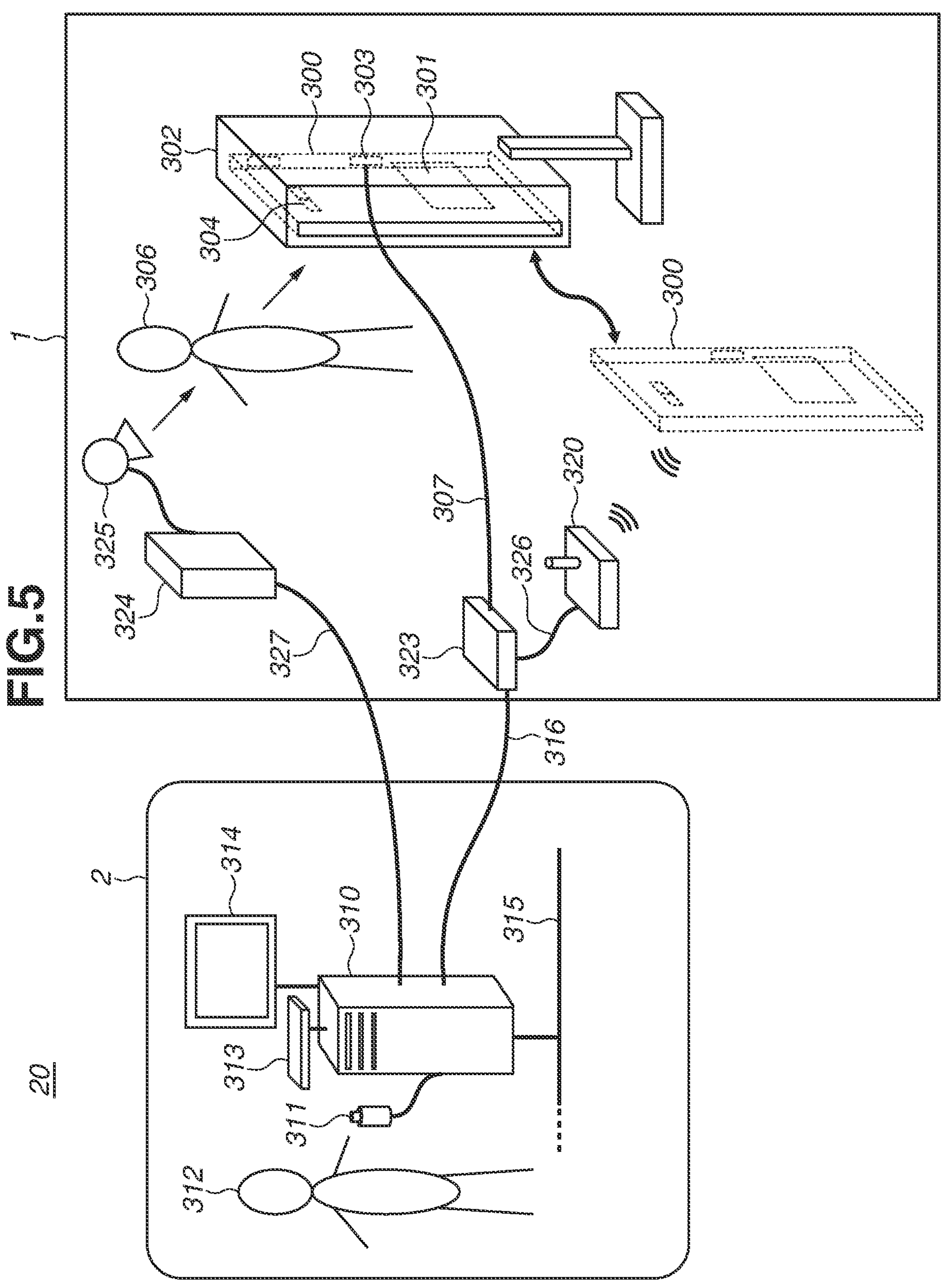
FIG. 5 is a diagram illustrating another configuration example of the radiographic system.

FIG. 5 is a diagram illustrating a configuration example of a radiographic system 20 according to another exemplary embodiment. The configuration of the radiographic system 20 illustrated in FIG. 5 is similar to the configuration of the radiographic system 10 illustrated in FIG. 1, with the addition of a radiation room communication cable 316, an access point (AP) 320, a communication control apparatus 323, and an AP communication cable 326. The AP 320, the communication control apparatus 323, and the AP communication cable 326 are installed in the radiation room 1.

The radiation room communication cable 316 connects the control apparatus 310 and the communication control apparatus 323. The AP communication cable 326 connects the communication control apparatus 323 and the AP 320. The radiographic imaging apparatus communication cable 307 connects the radiographic imaging apparatus 300 and the communication control apparatus 323.

The AP 320 performs wireless communication with the radiographic imaging apparatus 300. For example, when the radiographic imaging apparatus 300 is detached from the upright position stand 302 and used, the AP 320 relays communication between the radiographic imaging apparatus 300 and the control apparatus 310 and the radiation generating apparatus 324.

While FIG. 5 illustrates an example where the radiographic imaging apparatus 300 performs communication via the AP 320, the AP 320 may not necessarily be used. For example, in another exemplary embodiment, either the radiographic imaging apparatus 300 or the communication control apparatus 323 can operate as an access point, and the radiographic imaging apparatus 300 and the control apparatus 310 and the radiation generating apparatus 324 can directly communicate with each other.

The communication control apparatus 323 performs control so that the radiographic imaging apparatus 300, the AP 320, and the control apparatus 310 can communicate with each other.

Referring to FIG. 5, in a case where the radiographic imaging apparatus 300 is mounted in the upright position stand 302, the radiographic imaging apparatus 300 communicates with the control apparatus 310 via the wired communication unit 303, the radiographic imaging apparatus communication cable 307, the communication control apparatus 323, and the radiation room communication cable 316.

In a case where the radiographic imaging apparatus 300 is detached from the upright position stand 302, the radiographic imaging apparatus 300 communicates with the control apparatus 310 via the wireless communication unit 304, the AP 320, the AP communication cable 326, the communication control apparatus 323, and the radiation room communication cable 316.

FIG. 5 illustrates the example using the configuration where the radiation generating apparatus communication cable 327 is directly connected to the control apparatus 310, but this configuration is not limited thereto. In another exemplary embodiment, the radiation generating apparatus communication cable 327 can be connected to the communication control apparatus 323, and the radiation generating apparatus 324 and the control apparatus 310 can communicate with each other via the communication control apparatus 323.

As described above, the radiographic system 10 and the radiographic system 20 include the radiation generating apparatus 324, the control apparatus 310, and the radiographic imaging apparatus 300. The radiation generating apparatus 324 controls irradiation with radiation from the radiation source 325. The radiographic imaging apparatus 300 captures an image based on the radiation from the radiation source 325.

As described above, in step S102, the radiographic imaging apparatus 300 receives the imaging condition information and the automatic exposure control information from the radiation generating apparatus 324 or the control apparatus 310. The automatic exposure control information is the AEC information. The radiographic imaging apparatus 300 can generate the radiation irradiation stop signal in step S107 based on the automatic exposure control information. The radiation generating apparatus 324 receives the imaging condition information and the automatic exposure control information from the control apparatus 310, and controls the irradiation with the radiation from the radiation source 325 based on the imaging condition information and the automatic exposure control information.

The above-described automatic exposure control information includes one or more of information about whether the automatic exposure control function is used, a density in automatic exposure control, sensitivity in the automatic exposure control, receptor field information in the automatic exposure control, or a target dose in the automatic exposure control.

The above-described imaging condition information includes one or more of body part information of the subject 306, a tube voltage, a tube current, an irradiation time, a maximum permissible irradiation time, physical size information, a focal length, or setting information about automatic exposure control.

In step S107, the radiation generating apparatus 324 and the radiographic imaging apparatus 300 communicate irradiation control information for controlling the irradiation with the radiation from the radiation source 325 based on the dose of the radiation from the radiation source 325 with each other. The irradiation control information is, for example, the radiation irradiation stop signal. More specifically, the radiographic imaging apparatus 300 detects the radiation from the radiation source 325, and transmits the radiation irradiation stop signal to the radiation generating apparatus 324 based on the dose of the detected radiation. Upon receiving the radiation irradiation stop signal, the radiation generating apparatus 324 performs control to stop the radiation irradiation from the radiation source.

In steps S104 and S108, the radiation generating apparatus 324 and the radiographic imaging apparatus 300 communicate synchronization information for synchronizing imaging timing between the radiation generating apparatus 324 and the radiographic imaging apparatus 300 with each other. The synchronization information communicated in step S104 is synchronization start information communicated between the radiation generating apparatus 324 and the radiographic imaging apparatus 300 before start of radiation irradiation. The synchronization information communicated in step S108 is synchronization end information communicated between the radiation generating apparatus 324 and the radiographic imaging apparatus 300 after the start of radiation irradiation.

In step S110, the radiation generating apparatus 324 transmits actual exposure condition information (actual exposure information) and radiation dose information (dose information) to the control apparatus 310. The above-described actual exposure condition information includes one or more of a tube voltage, a tube current, an irradiation time, a tube current-time product, a focal point-to-subject distance, or a focal point-to-detector distance. The above-described radiation dose information includes one or more of an irradiation dose, an absorbed dose, an area dose, air kerma, or a skin dose.

The radiation generating apparatus 324 and the radiographic imaging apparatus 300 perform the communications in steps S102, S104, S107, S108, and S110 using the same interface. The radiation generating apparatus 324 and the radiographic imaging apparatus 300, which are illustrated in FIG. 1, perform the communications in steps S102, S104, S107, S108, and S110 via the control apparatus 310 using the same interface.

The radiographic imaging apparatus 300 performs the communications in steps S102, S104, S107, S108, and S110 using the same interface. The radiation generating apparatus 324 and the control apparatus 310 perform the communications in steps S102, S104, S107, S108, and S110 using the same interface. The radiographic imaging apparatus 300 and the control apparatus 310 perform the communications in steps S102, S104, S107, S108, and S110 using the same interface.

As described above, the interface is a wired communication interface or a wireless communication interface, and is, for example, the wired communication unit 303 or the wireless communication unit 304. The communication using the interface is controlled by execution of a program.

As described above, the radiographic system 10 performs the communications in steps S102, S104, S107, S108, and S110 using the same interface. This enables saving effort and cost for modifications. The radiographic system 10 eliminates the need to separately provide a communication interface for synchronization information and a communication interface for automatic exposure control. The radiation generating apparatus 324 is connectable to the radiographic imaging apparatus 300 having the automatic exposure control function without a communication interface for automatic exposure control separate from the communication interface for synchronization information.

An exemplary embodiment of the present disclosure enables communication for automatic exposure control without adding an interface.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, these embodiments are not seen to be limiting. The scope of the following claims is to be accorded the broadest interpretation so as to encompass all such modifications and equivalent structures and functions.

This application claims the benefit of Japanese Patent Application No. 2022-067007, filed Apr. 14, 2022, which is hereby incorporated by reference herein in its entirety.

What is claimed is:

1. A radiographic system comprising:

a radiation generating apparatus configured to control irradiation with radiation from a radiation source; and a radiographic imaging apparatus configured to capture an image based on the radiation from the radiation source, wherein the following communications are performed using a same interface: (1) communication of irradiation control information for controlling the irradiation from the radiation source based on a dose of the radiation emitted from the radiation source, (2) communication of synchronization information for synchronizing imaging timing between the radiation generating apparatus and the radiographic imaging apparatus, and (3) communication of automatic exposure control information between the radiation generating apparatus and the radiographic imaging apparatus, and wherein the irradiation control information is a radiation irradiation stop signal, and the radiation irradiation stop signal is a signal generated based on the automatic exposure control information.

2. The radiographic system according to claim 1, wherein the synchronization information is synchronization start information communicated between the radiation generating apparatus and the radiographic imaging apparatus before start of the irradiation with the radiation.

3. The radiographic system according to claim 1, wherein the synchronization information is synchronization end information communicated between the radiation generating apparatus and the radiographic imaging apparatus after start of the irradiation with the radiation.

4. The radiographic system according to claim 1, wherein the same interface is a wired communication interface or a wireless communication interface.

5. The radiographic system according to claim 1, wherein the automatic exposure control information includes at least one of information about whether an automatic exposure control function is used, a density in automatic exposure control, sensitivity in the automatic exposure control, receptor field information in the automatic exposure control, or a target dose in the automatic exposure control.

6. The radiographic system according to claim 1, further comprising a control apparatus configured to control aspects of the radiographic system, wherein the radiographic imaging apparatus is configured to receive imaging condition information from the radiation generating apparatus or the control apparatus, and wherein the radiographic imaging apparatus is configured to perform the communication of the irradiation control information, the communication of the synchronization information, and the reception of the imaging condition information using the same interface.

7. The radiographic system according to claim 6, wherein the imaging condition information includes at least one of body part information of a subject, a tube voltage, a tube current, an irradiation time, a maximum permissible irradiation time, physical size information, a focal length, or setting information about automatic exposure control.

8. The radiographic system according to claim 1, wherein the communication of the irradiation control information, the communication of the synchronization information, and the communication of the automatic exposure control information are performed between the radiation generating apparatus and the radiographic imaging apparatus via a control apparatus using the same interface.

9. The radiographic system according to claim 8, wherein the radiation generating apparatus is configured to transmit actual exposure condition information to the control apparatus, and wherein the radiation generating apparatus and the control apparatus are configured to perform the communication of the irradiation control information, the communication of the synchronization information, the communication of the automatic exposure control information, and communication of the actual exposure condition information between each other using the same interface.

10. The radiographic system according to claim 9, wherein the actual exposure condition information includes at least one of a tube voltage, a tube current, an irradiation time, a tube current-time product, a focal point-to-subject distance, or a focal point-to-detector distance.

11. The radiographic system according to claim 8, wherein the radiation generating apparatus is configured to transmit radiation dose information to the control apparatus, and wherein the radiation generating apparatus and the control apparatus are configured to perform the communication of the irradiation control information, the communication of the synchronization information, the communication of the automatic exposure control information, and communication of the radiation dose information between each other using the same interface.

12. The radiographic system according to claim 11, wherein the radiation dose information includes at least one of an irradiation dose, an absorbed dose, an area dose, air kerma, or a skin dose.

13. The radiographic system according to claim 8, wherein the radiation generating apparatus is configured to receive imaging condition information and the automatic exposure control information from the control apparatus, wherein the radiation generating apparatus is configured to control the irradiation with the radiation from the radiation source based on the imaging condition information and the automatic exposure control information, wherein the radiation generating apparatus is configured to transmit actual exposure condition information and radiation dose information to the control apparatus, and wherein the radiation generating apparatus and the control apparatus are configured to perform the communication of the irradiation control information, the communication of the synchronization information, communication of the imaging condition information, the communication of the automatic exposure control information, communication of the actual exposure condition information, and communication of the radiation dose information between each other using the same interface.

14. A method for controlling a radiographic system including a radiation generating apparatus configured to control irradiation with radiation from a radiation source and a radiographic imaging apparatus configured to capture an image based on the radiation from the radiation source, the method comprising:

performing the following communications using a same interface: (1) communication of irradiation control information for controlling the irradiation from the radiation source based on a dose of the radiation emitted from the radiation source, (2) communication of synchronization information for synchronizing imaging timing between the radiation generating apparatus and the radiographic imaging apparatus, and (3) communication of automatic exposure control information between the radiation generating apparatus and the radiographic imaging apparatus, wherein the irradiation control information is a radiation irradiation stop signal, and the radiation irradiation stop signal is a signal generated based on the automatic exposure control information.

* * * * *